United States Patent [19]

Nagata et al.

[11] Patent Number: 5,295,389
[45] Date of Patent: Mar. 22, 1994

[54] THERMAL CONDUCTIVITY DETECTOR

[75] Inventors: Mitsuhiko Nagata; Shoji Kamiunten, both of Kanagawa; Tatsuyuki Uchida; Misako Seita, both of Tokyo, all of Japan

[73] Assignee: Yamatake-Honeywell Co., Ltd., Japan

[21] Appl. No.: 923,138

[22] Filed: Jul. 31, 1992

[30] Foreign Application Priority Data

Aug. 21, 1991 [JP] Japan .................. 3-232461

[51] Int. Cl.⁵ .................. G01N 31/00; H01C 7/10
[52] U.S. Cl. .................. 73/25.03; 422/98; 374/135; 338/24; 338/25
[58] Field of Search .................. 73/25.03, 23.25, 23.26, 73/204.26, 204.23, 204.25; 374/135; 422/98

[56] References Cited

U.S. PATENT DOCUMENTS

| 4,471,647 | 9/1984 | Jerman et al. ........... 374/135 X |
| 4,501,144 | 2/1985 | Higashi et al. ........... 73/204 |
| 4,542,650 | 9/1985 | Renken et al. ........... 73/204 |
| 4,581,928 | 4/1986 | Johnson ........... 73/204 |
| 4,784,721 | 11/1988 | Holmen et al. ........... 156/647 X |
| 4,914,742 | 4/1990 | Higashi et al. ........... 73/204 |
| 5,050,429 | 9/1991 | Nishimoto et al. ........... 73/204.26 |

FOREIGN PATENT DOCUMENTS

| 0107923 | 4/1990 | Japan ........... 73/204.25 |
| 4-072523 | 3/1992 | Japan ........... 73/204.25 |

Primary Examiner—Robert J. Warden
Assistant Examiner—E. Leigh Dawson
Attorney, Agent, or Firm—Whitham & Marhoefer

[57] ABSTRACT

A thermal conductivity detector includes a thin diaphragm, a heat-generating portion, and a pair of boundary holes. The thin diaphragm is obtained by forming a space in part of a base. The heat-generating portion is formed in the diaphragm. The boundary holes are formed to surround the heat-generating portion.

15 Claims, 4 Drawing Sheets

THERMAL CONDUCTIVITY DETECTOR

BACKGROUND OF THE INVENTION

The present invention relates to a thermal conductivity detector which is used for a gas chromatograph for performing gas analysis by utilizing the difference in adsorptivity between a filler and a gas filled in, e.g., a column, and is designed to detect the thermal conductivity of the gas so as to perform the gas analysis.

In a petrochemical process, a steel process, or the like, a gas chromatograph has been generally used as an analyzer for analyzing the components of a process gas, monitoring each step in a process on the basis of the analysis result, and performing various types of control operations.

In such a gas chromatograph, a column is filled with a powder, as a stationary phase, such as active carbon, active alumina, or molecular sieves having a uniform grain size. The type of powder differs depending on the sample gas. The components of a sample gas are separated from each other by utilizing the difference in moving rate based on the difference in adsorptivity or the difference in distribution coefficient between the stationary phase and each component of the sample gas. Each component is then detected by a detector such as a thermal conductivity detector (TCD).

As such a thermal conductivity detector, a temperature-sensitive element such as a thermistor has been used. A small integrated detector has recently been proposed by Jhon H. Jerman et al. (U.S. Pat. No. 4,471,647).

This detector is constituted by an elongated metal film resistor, a membrane holding the metal film resistor and having a plurality of holes to allow a gas to flow on both the sides of the membrane, and a means for holding the membrane and the metal film resistor These thermal conductivity detectors are driven by, e.g., a constant current to detect the ratios of different types of gases by detecting differences in heat radiation ratio from the detectors into the gases, caused by differences in thermal conductivity between the gases, in terms of voltages.

In the detector disclosed in U.S. Pat. No. 4,471,647, since a plurality of holes are formed in the membrane at positions near the detector terminals to allow a gas to flow on both the sides of the membrane, when the gas flows on both the sides of the membrane, the detector may be adversely affected by the gas flows to cause an error or may detect disturbance of the flow, resulting in measurement error. In addition, since a large amount of heat generated by the detector is dissipated between the membrane and the means for holding the membrane, accurate measurement cannot be performed. Furthermore, when particles such as dust and mist particles are trapped in the plurality of holes, the detection sensitivity of the sensor deteriorates.

SUMMARY OF THE INVENTION

The present invention, therefore, has been made to solve the conventional problems, and has as its object to provide a high-sensitivity, high-reliability thermal conductivity detector which has a means for supplying a gas to both sides of a diaphragm and is resistant to the influences of gas flows.

In order to achieve the above object, according to the first aspect of the present invention, there is provided a thermal conductivity detector comprising a thin diaphragm obtained by forming a space in part of a base, a heat-generating portion formed in the diaphragm, and a pair of slit-like boundary holes formed to surround the heat-generating portion.

According to the second aspect of the present invention, there is provided a thermal conductivity detector comprising a thin diaphragm obtained by forming a space in part of a base, a heat-generating portion formed in the diaphragm, and two pairs of slit-like boundary holes formed to surround the heat-generating portion.

According to the third aspect of the present invention, there is provided a thermal conductivity detector comprising a thin diaphragm obtained by forming a space in part of a base, a heat-generating portion formed in the diaphragm, and a plurality of slit-like boundary holes formed to surround the heat-generating portion.

According to still another aspect of the present invention, there is provided a thermal conductivity detector further comprising a plurality of slits outside the respective slit-like boundary holes.

According to the present invention, since the boundary holes are formed in the diaphragm between the heat-generating portion and the base, the thermal insulating property of the heat-generating portion with respect to the base is improved to allow high-precision measurement. In addition, since a gas flows into a portion below the diaphragm through the boundary holes separated from the heat-generating portion and the slits formed outside the boundary holes, even if dust particles and the like are mixed in, they do not adhere to portions near the heat-generating portion, and the flow of the gas near the heat-generating portion is less disturbed, thereby allowing high-precision measurement over a long period of time.

DESCRIPTION OF THE PREFERRED EMBODIMENTS

Embodiments of the present invention will be described in detail below with reference to the accompanying drawings.

Figure 1:
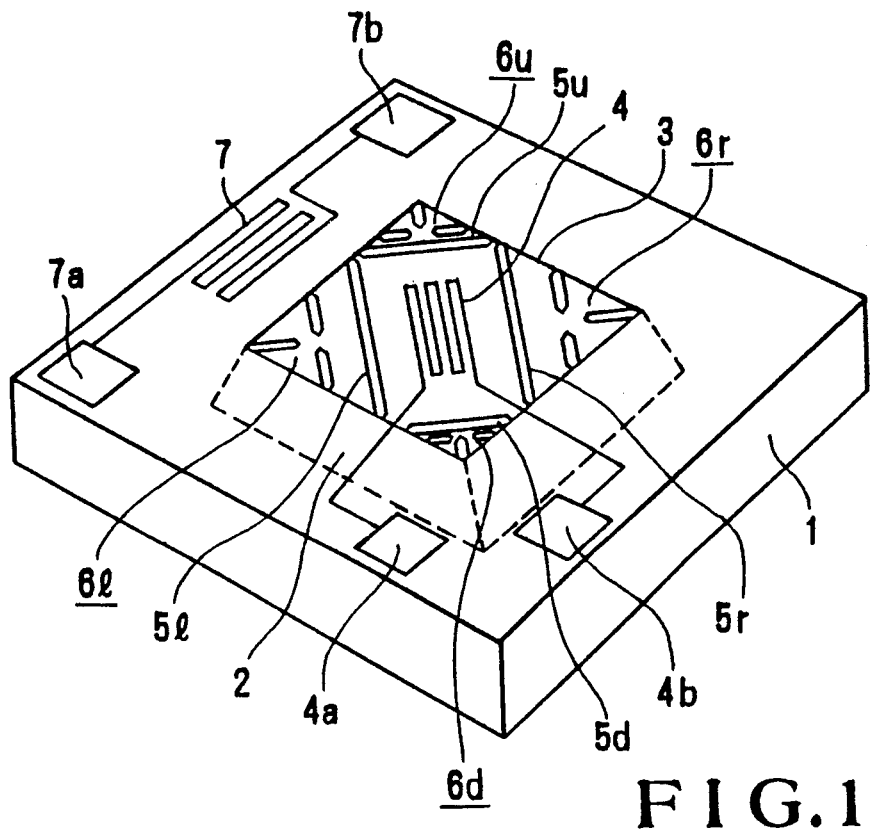
FIG. 1 is a perspective view showing the arrangement of a thermal conductivity detector according to an embodiment of the present invention.

FIG. 1 shows the arrangement of a thermal conductivity detector according to an embodiment of the present invention. Referring to FIG. 1, reference numeral 1 denotes a semiconductor substrate made of, e.g., silicon and serving as a base. An opening portion 2 having a trapezoidal cross-section is formed in a central portion of the lower surface of the semiconductor substrate 1 by, e.g., anisotropic etching so as not to communicate with the upper surface of the semiconductor substrate 1. A thin diaphragm 3 is integrally formed on the bottom side of the opening portion 2, i.e., the upper surface side of the semiconductor substrate 1. In addition, a thin heater element 4 is formed on a central portion of the upper surface of the diaphragm 3 by a normal thin film formation technique. Heater terminals 4a and 4b of the heater element 4 are formed at a thick portion of the semiconductor substrate 1.

Figure 2:
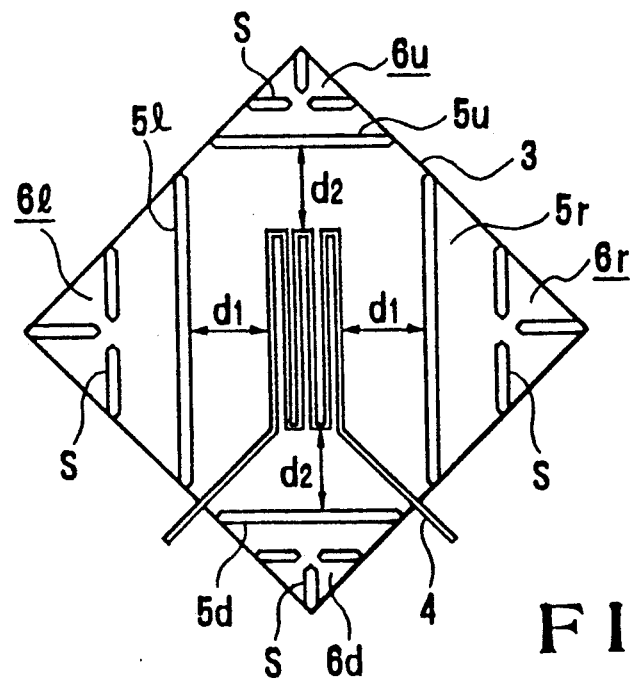
FIG. 2 is a plan view showing the arrangement of a diaphragm in FIG. 1.

As shown in the enlarged plan view of FIG. 2, parallel slit-like boundary holes 5l and 5r are formed on the left and right sides of the heater element 4 at a predetermined distance $d_1$ therefrom. The boundary holes 5l and 5r are formed along the longitudinal direction of the heater element 4 to extend through a thin portion of the diaphragm 3. In addition, slit portions 6l and 6r obtained by forming a plurality of slits S extending through this thin portion are respectively formed at corners, of the diaphragm 3, located outside the boundary holes 5l and 5r. Similarly, parallel slit-like boundary holes 5u and 5d are formed on the upper and lower sides of the heater element 4 at a predetermined distance $d_2$ therefrom. These boundary holes 5u and 5d are formed along the widthwise direction of the heater element 4 to extend through the thin portion of the 7 diaphragm 3. In addition, slit portions 6u and 6d obtained by forming a plurality of slits S extending through the thin portion are respectively formed at corners, of the diaphragm 3, located outside the boundary holes 5u and 5d.

That is, the diaphragm 3 is constituted by a first diaphragm $3_1$ defined by the slit-like boundary holes 5l, 5r, 5u, and 5d, on which no slits S are formed but only the heater element 4 is formed, and a second diaphragm $3_2$ on which the slit portions 6l, 6r, 6u, and 6d, each having a plurality of slits S, are formed. The second diaphragm $3_2$ is held by the thick portion of the semiconductor substrate 1. Note that these boundary holes 5l, 5r, 5u, and 5d and the slits S of the slit portions 6l, 6r, 6u, and 6d can be easily formed by normal photolithography or a wet or dry etching technique. In addition, as shown in FIG. 1, a thin temperature-measuring resistive element 7 for detecting the temperature of a gas is formed on the thick portion of the semiconductor substrate 1. Reference numerals 7a and 7b denote electrode terminals of the element 7.

With this arrangement, the diaphragm 3 has the following advantages. Since the heater element 4 is formed on the first diaphragm $3_1$, and the slit portions 6l and 6r are formed on the second diaphragm $3_2$ through the boundary holes 5l and 5r, i.e., no slits and holes are formed in the diaphragm $3_1$, when a gas to be measured passes through the heat-generating portion, its flow is not disturbed by slits or the like. If the heater element 4 is driven by a constant-current scheme, a constant-voltage scheme, a constant-temperature scheme, a small temperature difference scheme, or the like, changes in thermal conductivity among different types of gases can be stably measured in terms of resistance changes, voltage changes, power changes, or the like.

In addition, with this arrangement, the diaphragm 3 has the following advantages. Since the heater element 4 is formed on the first diaphragm $3_1$, and the slit portions 6l and 6r are formed on the second diaphragm $3_2$ through the boundary holes 5l and 5r, a gas to be measured can flow into the diaphragm 3 through the boundary holes 5l and 5r and the slit portions 6l and 6r formed on the diaphragm $3_2$ thus replacing any residual gas in the diaphragm 3. Furthermore, since no slits, holes, and the like are formed in the diaphragm $3_1$, as described above, no flow disturbance occurs, and dust and mist particles do not easily adhere to the diaphragm $3_1$, thus allowing more stable measurement. Moreover, since the diaphragm $3_1$ is thermally insulated from the second diaphragm $3_2$ and the thick portion of the semiconductor substrate 1 through the boundary holes 5l, 5r, 5u, and 5d, the amount of heat transferred to the semiconductor substrate 1 is greatly reduced. That is, since the heater element 4 is almost completely thermally insulated from the semiconductor substrate 1, high-sensitivity, high-precision detection can be performed by using the heater element 4 with low power consumption.

Note that the predetermined distances $d_1$ and $d_2$ from the left and right sides and from the upper and lower sides of the heater element 4 are distances at which thermal insulation of the heater element 4 can be ensured, and measurement can be performed without being influenced by dust or mist particles adhering to portions near the boundary holes 5l, 5r, 5u, and 5d, e.g., about ½ the width of the heater element 4.

Figure 3:
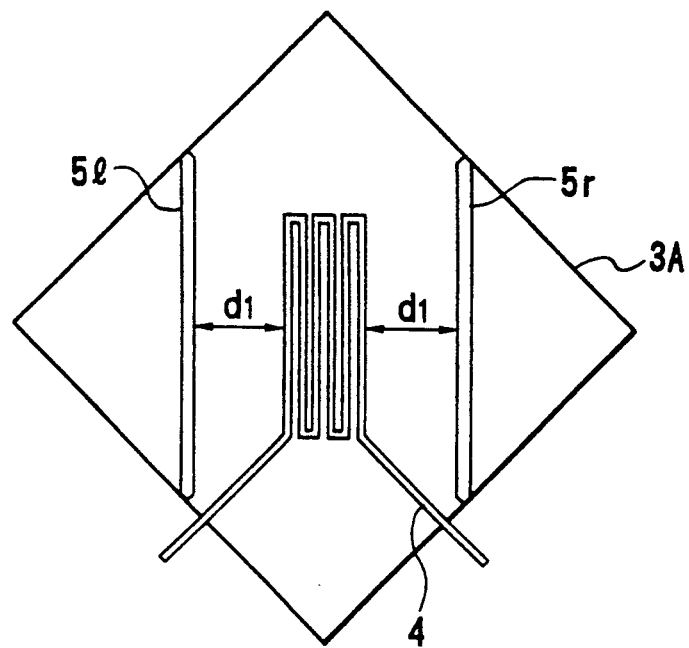
FIG. 3 is a plan view showing the arrangement of a diaphragm according to another embodiment of the present invention.
Figure 4:
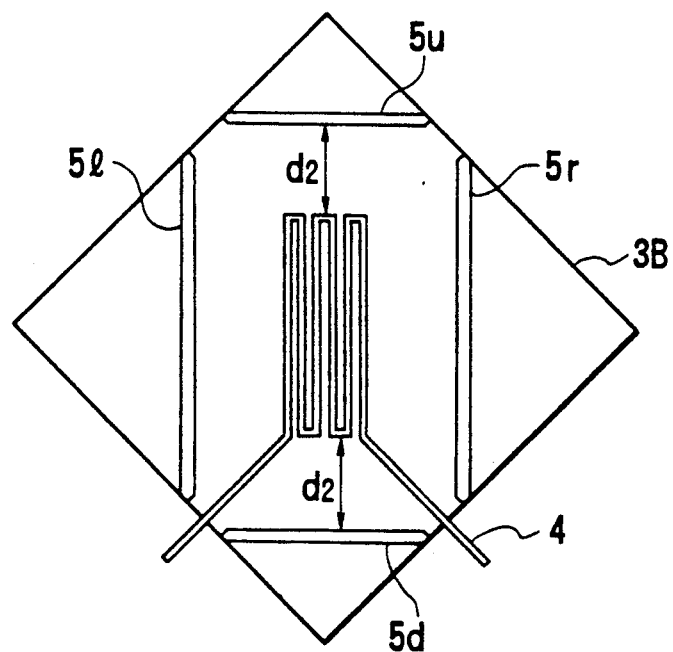
FIG. 4 is a plan view showing the arrangement of a diaphragm according to still another embodiment of the present invention.
Figure 5:
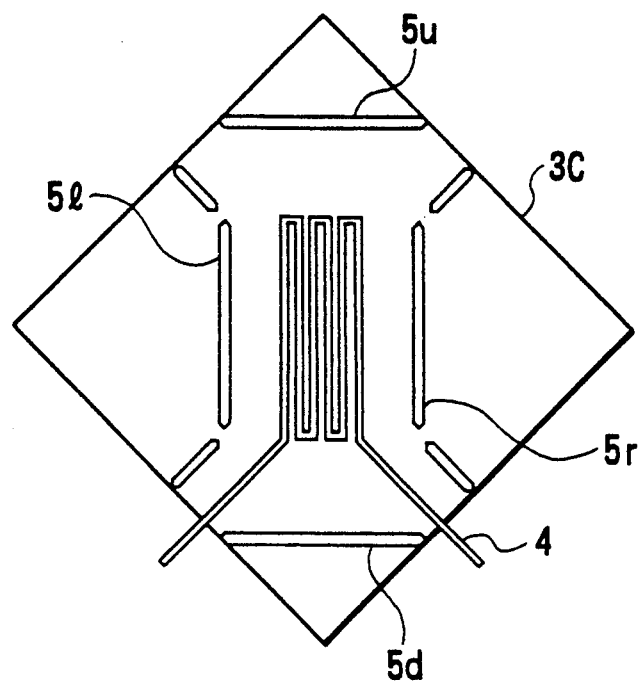
FIG. 5 is a plan view showing the arrangement of a diaphragm according to still another embodiment of the present invention.
Figure 6:
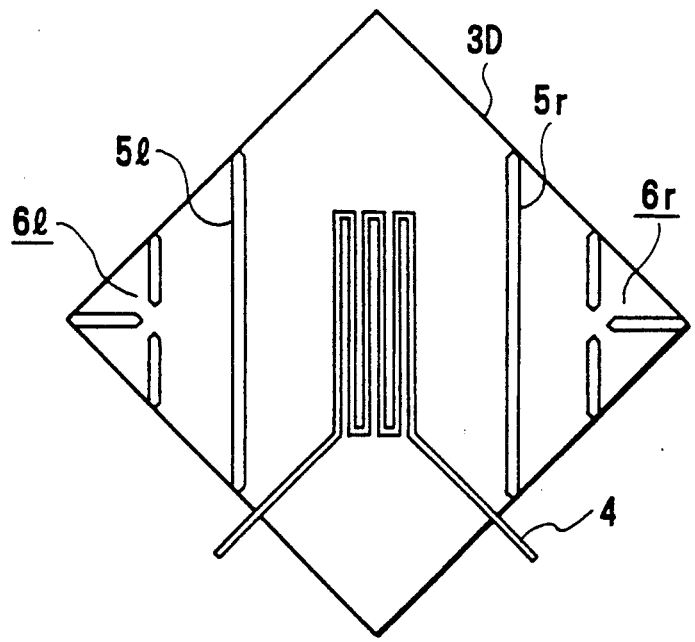
FIG. 6 is a plan view showing the arrangement of a diaphragm according to still another embodiment of the present invention.
Figure 7:
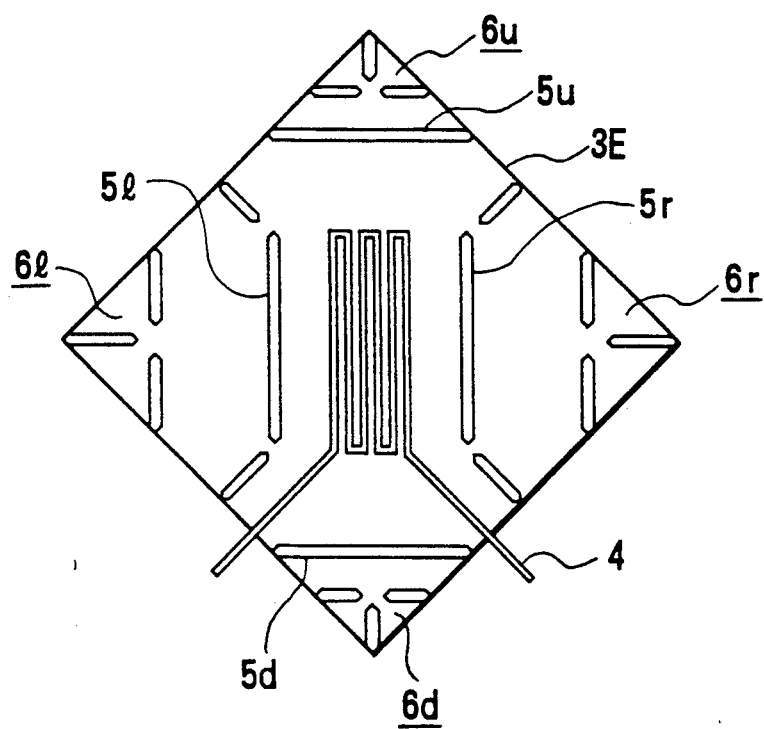
FIG. 7 is a plan view showing the arrangement of a diaphragm according to still another embodiment of the present invention.

In the above-described embodiment, the arrangement of the diaphragm 3 is not limited to the one shown in FIG. 2. For example, as shown in FIG. 3, parallel slit-like boundary holes 5l and 5r may be formed on the left and right sides of a heater element 4 at a predetermined distance $d_1$ therefrom to extend along the longitudinal direction of the element 4, thus forming a diaphragm 3A. In addition to the arrangement in FIG. 3, slit-like boundary holes 5u and 5d may be formed on the upper and lower sides of the heater element 4 at a predetermined distance $d_2$ therefrom to extend along the widthwise direction of the element 4, thus forming a diaphragm 3B, as shown in FIG. 4. Furthermore, as shown in FIG. 5, the two end portions of each of the slit-like boundary holes 5l and 5r shown in FIG. 4 may be bent outward to form a diaphragm 3C. As shown in FIG. 6, in addition to the arrangement in FIG. 3, slit portions 6l and 6r may be respectively formed outside the boundary holes 5l and 5r to form a diaphragm 3D. Moreover, as shown in FIG. 7, in addition to the arrangement in FIG. 5, slit portions 5l, 5r, 6u, and 6d may be respectively formed outside the boundary holes 5l and 5r and the slit portions 6l and 6r to form a diaphragm 3E.

In the above embodiment, anisotropic etching is performed from the lower surface side of the semiconductor substrate 1 to form the opening portion 2 in the semiconductor substrate 1. However, boundary holes 5l and 5r and a plurality of slits S may be formed in the diaphragm 3, and anisotropic or isotropic etching may be performed from the upper surface of the substrate 1 by utilizing the etching characteristics along the crystallographic axis so as to form a hollow portion below the diaphragm 3.

In the above-described embodiment, a semiconductor substrate made of, e.g., silicon is used as a base. However, the present invention is not limited to this. Even if, for example, a metal plate made of aluminum or stainless steel is used as a base, and the diaphragm 3 is made of an insulating film made of, e.g., $SiO_2$ or $Si_3N_4$, the same effects as those described above can be obtained.

In the above embodiment, anisotropic etching is performed to form the diaphragm 3. However, the same structure can be formed by other etching methods such as an isotropic etching method using, e.g., a solution mixture of nitric acid and hydrofluoric acid.

In addition, the method of forming the diaphragm 3 is not limited to etching. For example, it can be formed by a process using an end mill, a laser, or the like. Alternatively, the semiconductor substrate 1 and the diaphragm 3 may be separately formed to be bonded to each other afterward.

As has been described above, according to the thermal conductivity detector of the present invention, since its structure is not easily influenced by the flow of a gas, and dust, mist, and the like do not easily adhere thereto, changes in thermal conductivity can be stably measured with high precision.

What is claimed is:

1. A thermal conductivity detector comprising in combination:
    a substrate base with a cavity in said substrate base;
    a thin diaphragm extending over said cavity;
    a heater element formed on a central portion of said diaphragm, said heater element exhibiting a characteristic change in its electrical impedance as a function of the thermal conductivity of a fluid flow passing over said heater element;
    a plurality of boundary holes in said thin diaphragm, said boundary holes framing said heater element at a predetermined distance from said heater element to provide thermal isolation between the heater element and said base; and
    said predetermined distance being sufficient that particles adhering to said boundary holes have a minimal effect on fluid flow in the vicinity of said heater element.

2. A thermal conductivity detector as in claim 1, wherein said heater element has a dimension extending in a direction parallel to said fluid flow and said predetermined distance is approximately one-half said dimension of said heater element.

3. A thermal conductivity detector as in claim 2, wherein said plurality of boundary holes frame four sides of said heater element.

4. A thermal conductivity detector as in claim 3, wherein said plurality of boundary holes extend substantially to the substrate base.

5. A thermal conductivity detector as in claim 2 wherein said plurality of boundary holes extend substantially to the substrate base.

6. A thermal conductivity detector as in claim 1, wherein said plurality of boundary holes frame four sides of said heater element.

7. A thermal conductivity detector as in claim 6, wherein said plurality of boundary holes extend substantially to the substrate base.

8. A thermal conductivity detector as in claim 1, wherein said plurality of boundary holes extend substantially to the substrate base.

9. A thermal conductivity detector comprising in combination:
    a substrate base with a cavity in said substrate base;
    a thin diaphragm extending over said cavity;
    a heater element formed on a central portion of said diaphragm, said heater element exhibiting a characteristic change in its electrical impedance as a function of the thermal conductivity of a fluid flow passing over said heater element;
    a plurality of boundary holes in said thin diaphragm, said boundary holes framing said heater element at a predetermined distance from said heater element to provide thermal isolation between the heater element and said base;
    said predetermined distance being sufficient that particles adhering to said boundary holes have a minimal effect on fluid flow in the vicinity of said heater element; and
    a plurality of slits extending through said diaphragm in a region between said substrate base and said plurality of boundary holes.

10. A thermal conductivity detector as in claim 9, wherein said heater element has a dimension extending in a direction parallel to said fluid flow and said predetermined distance is approximately one-half said dimension of said heater element.

11. A thermal conductivity detector as in claim 10, wherein said plurality of boundary holes frame four sides of said heater element.

12. A thermal conductivity detector as in claim 11, wherein said plurality of boundary holes extend substantially to the substrate base.

13. A thermal conductivity detector as in claim 9, wherein said plurality of boundary holes frame four sides of said heater element.

14. A thermal conductivity detector as in claim 13, wherein said plurality of boundary holes extend substantially to the substrate base.

15. A thermal conductivity detector as in claim 9, wherein said plurality of boundary holes extend substantially to the substrate base.

* * * * *